United States Patent

Bal

[11] Patent Number: 6,019,993
[45] Date of Patent: Feb. 1, 2000

[54] VIRUS-INACTIVATED 2-COMPONENT FIBRIN GLUE

[75] Inventor: Frederic Bal, Vienna, Austria

[73] Assignee: Omrix Biopharmaceuticals S.A., Brussels, Belgium

[21] Appl. No.: 08/530,167

[22] PCT Filed: Mar. 27, 1994

[86] PCT No.: PCT/EP94/00966

§ 371 Date: Nov. 30, 1995

§ 102(e) Date: Nov. 30, 1995

[87] PCT Pub. No.: WO94/22503

PCT Pub. Date: Oct. 13, 1994

[30] Foreign Application Priority Data

Mar. 30, 1993 [EP] European Pat. Off. .............. 93105298

[51] Int. Cl.[7] .................. A61F 2/06; A61K 35/14
[52] U.S. Cl. .................. 424/426; 530/380; 530/381; 530/382; 530/383
[58] Field of Search .................. 424/426; 530/380, 530/381, 382, 383

[56] References Cited

FOREIGN PATENT DOCUMENTS

| | | |
|---|---|---|
| 0 116 263 | 1/1986 | European Pat. Off. . |
| 0 339 607 | 4/1989 | European Pat. Off. . |
| 0 534 178 | 3/1993 | European Pat. Off. . |
| 2 201 993 | 1/1972 | Germany . |
| 2 102 811 | 2/1983 | United Kingdom . |
| PCTUS8501695 | 9/1985 | WIPO . |
| PCTCH9200036 | 2/1992 | WIPO . |
| PCT/SE92/00441 | 6/1992 | WIPO . |
| PCTEP9301797 | 7/1993 | WIPO . |

*Primary Examiner*—Carlos Azpuru
*Attorney, Agent, or Firm*—Jacobson, Price, Holman, & Stern, PLLC

[57] ABSTRACT

A two-component fibrin glue for human application includes a) a component A containing i) a virus-inactivated and concentrated cryoprecipitate that contains fibrinogen, and ii) tranexamic acid or a pharmaceutically acceptable salt, thereof; and b) component B containing a proteolytic enzyme that, upon combination with component A, cleaves, specifically, fibrinogen present in the cryoprecipitate of component A, thereby, effecting a fibrin polymer.

20 Claims, 3 Drawing Sheets

TISSEEL
SEM x 6.000

OCTACOL
SEM x 10.000

VIRUS-INACTIVATED 2-COMPONENT FIBRIN GLUE

This invention relates to a fibrin glue comprising two components A and B, a process for preparing the fibrin glue and the use of tranexamic acid and/or a substance having gelling properties or pharmaceutically acceptable salts thereof in a fibrin glue.

BACKGROUND

The European patent application EP 92 114 942 suggests an improved fibrin glue for surgical wound application or treatment of hemophilics. This fibrin glue contains a high amount of aprotinin which is the preferred protease inhibitor according to EP 92 114 942. Further there is suggested the use of snake venom derived proteolytic enzymes, preferably the compound batroxobin. It is advantageous to apply such a fibrin glue in order to treat also people having developed immunogenic reactions against thrombin with a fibrin glue The European patent application 92 112 295 suggests a fibrin glue which comprises additionally ingredients for culturing embryonic cells of mammals in one or both of the components A and B of the fibrin glue. Also this specific fibrin glue for in vitro fertilization contains aprotinin as preferred clinically accepted protease inhibitor.

EP-0 339 607 A2 is concerned with a composition for repair of cartilage and bone and method for their preparation as skeletal tissue implant. For this purpose the implantation of cells expressing a chondrocyte phenotype ($80 \times 10^6$ cells/ml), namely bone marrow derived chondrocytes or osteoblasts of autologous or homologous origin or homologous committed chondrocytes or autologous or homologous muscle fibroblast derived chondrocytes or any other progenital cells from mesenchymal origin is used. These cells are embedded in a biodegradable, biocompatible, biological resorbable immobilization vehicle (BRIV) adhesive glue consisting of fibrinogen, thrombin, $CaCl_2$, protease inhibitor, and at least 10%, preferably 15–30%, serum. As suitable protease inhibitors epsilon-aminocaproic acid and tranexamic acid are mentioned.

WO-A-92/22312 is concerned with a tissue treatment composition, especially an adhesive composition comprising fibrin or fibrinogen and a biodegradable and biocompatible polymer capable of forming a viscous aqueous solution. In addition to glueing, the tissue adhesive composition may be used for slow-release of a drug incorporated into it or for anti-adherence purposes, for wound healding, etc. One of these polymers is identified as the proteoglycan hyaluronic acid.

GB-A-2 102 811 deals with a tissue adhesive and a method of producing the same. The adhesive contains factor VIII, fibrinogen and an antibiotic.

WO-A-86/01814 discloses a fibrin adhesive prepared as a concentrate from single donor fresh frozen plasma. It does not deal with pool plasma fractions.

WO-A-92/15341 is dealing with an adhesive for bonding biological tissue in particular human body tissue. The adhesive contains fibrinogen, a substance capable of supplying calcium ions, blood-coagulating factor XIIIa and, as a fibrinogen-splitting substance, a snake-venom enzyme.

EP-A-0 166 263 discloses a filler composition for filling in defect or hollow portion of bone and kit or set for the preparation of the filler composition. The filler composition comprises fibrin and a calcium phosphate compound.

DE-A-22 01 993 discloses an enzyme preparation and a process for production of the same. The enzyme disclosed is a protease having thrombolytic activity and has been isolated from the snake venom of the snake bothrops.

Aprotinin is a quite common protease inhibitor. Chemically this compound is a polypeptide of 58 amino acids and is predominantly prepared from mammalian origin like bovine organs. Aprotinin is occuring in pankreatic, lung, liver, spleen cells. It inhibits plasmin, trypsin, chymotrypsin and other kininogenases. In therapy it is used to treat severe bleeding or treatment of shock.

However, also aprotinin may be immunogenic. Moreover, since most of the aprotinin is of bovine origin and some virus contamination has been reported further use of aprotinin is not entirely harmless.

The fibrin clot formed by the fibrin glues of prior art often dries out during ageing and turns into a hard and knife-sharp clot which may injure tissue if in motion.

SUMMARY OF THE INVENTION

Therefore, it is an object of the present invention to provide a fibrin glue having improved properties. Moreover, the fibrin glue should have little immunogenic properties and/or positive mechanical or handling properties.

Surprisingly, it has been found that a fibrin glue according to the invention solves the problems addressed above. Further, the addition of tranexamic acid has the added benefit of prolonging the duration of the clot in the tissue. Tranexamic acid which is 4-(aminomethyl)cyclohexane carboxylic acid (Tradename Hexakapron) can be used as substitution for aprotinin of prior art. In the following the term "tranexamic acid" also means the respective pharmaceutically acceptable salts.

The fibrin glue of the invention comprises a component A which comprises a cryoprecipitate of whole blood and a sufficient amount of tranexamic acid [4-(aminomethyl) cyclohexane carboxylic acid] or its pharmaceutically acceptable salts and a component B comprising a proteolytic enzyme being capable of cleaving specifically fibrinogen present in component A thereby causing the formation of a fibrin polymer.

Figure 1:
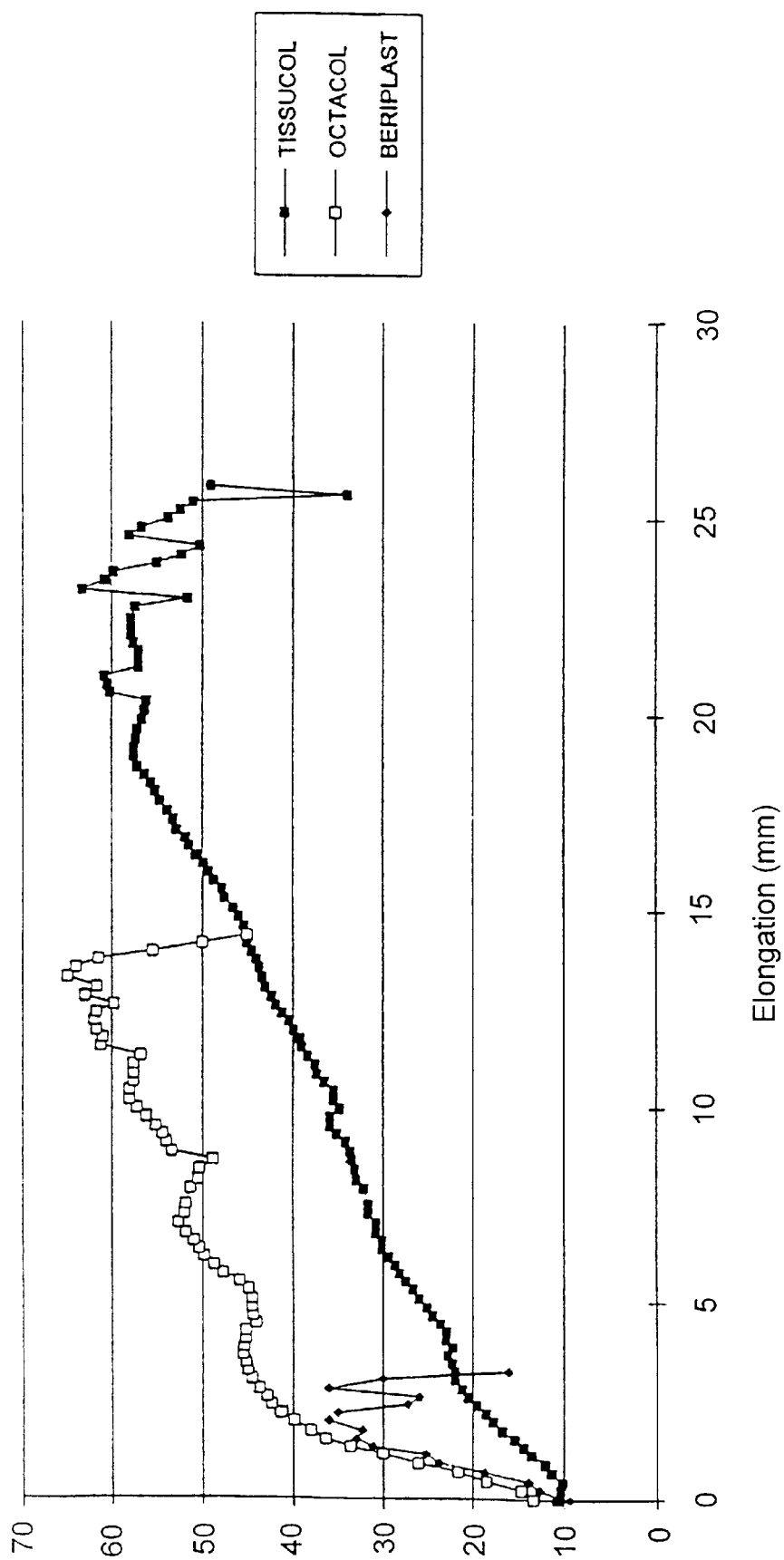
FIG. 1 is a graph of tensile strength vs. elongation comparing the instant invention with a commercial product.

The advantageous effects of the cryoprecipitate used according to the invention compared to fibrinogen enriched components A of prior art can be derived from FIG. 1. The commercial product Tissucol (curve 1) and Beriplast (curve 3) were measured with regard to their tensile strength versus elongation in comparison with the glue of the invention. Beriplast on the one hand showed initially a good behaviour by a given resistance against elongation of the clot formed but at higher tensile force it breaks at an elongation about 3 mm. This means that the Beriplast clot is very inflexible compared to the others.

On the other hand Tissucol is elongated already markedly at very low tensile force but breaks at very high elongation which is achieved with about 50 to 60 g tensile force. Such a behaviour is disadvantageous since a relatively small force leads already to a severe drawback: the glue does not adhere the opposite walls of a wound tightly. The wound is strechted and the walls of the wound are drifting away from each other upon the impact of mechanical stress. Since the walls of the wound are not fixed any more wound healing may be complicated or retarded.

The Beriplast is inconvenient because it is not flexible enough so that it breaks. The walls of the wound are also not any longer fixed.

Thus the glues of prior art give the surgeon only the two alternatives:

i) Beriplast relatively tough and rigid and able to fix the walls of a wound but then breaking at a low level of mechanical stress and ii) Tissucol relatively soft and viscous being flexible but low power of fixing walls of a wound.

The tissue glue of the invention using as component A cryoprecipitate, however, shows an advantageous behaviour. The fibrin glue of the invention provides a more ideal alternative. The tissue glue of the invention using a component A comprising cryoprecipitate and hexacapron compromize between the alternatives of prior art. Surprisingly, the tissue glue of the invention combines both the advantageous of Beriplast and Tissucol but avoids the drawbacks which are for Beriplast breaking of the clot at low elongation and for Tissucol the disadvantage of being too soft and not preventing the drift of the walls of a wound.

Figure 2:
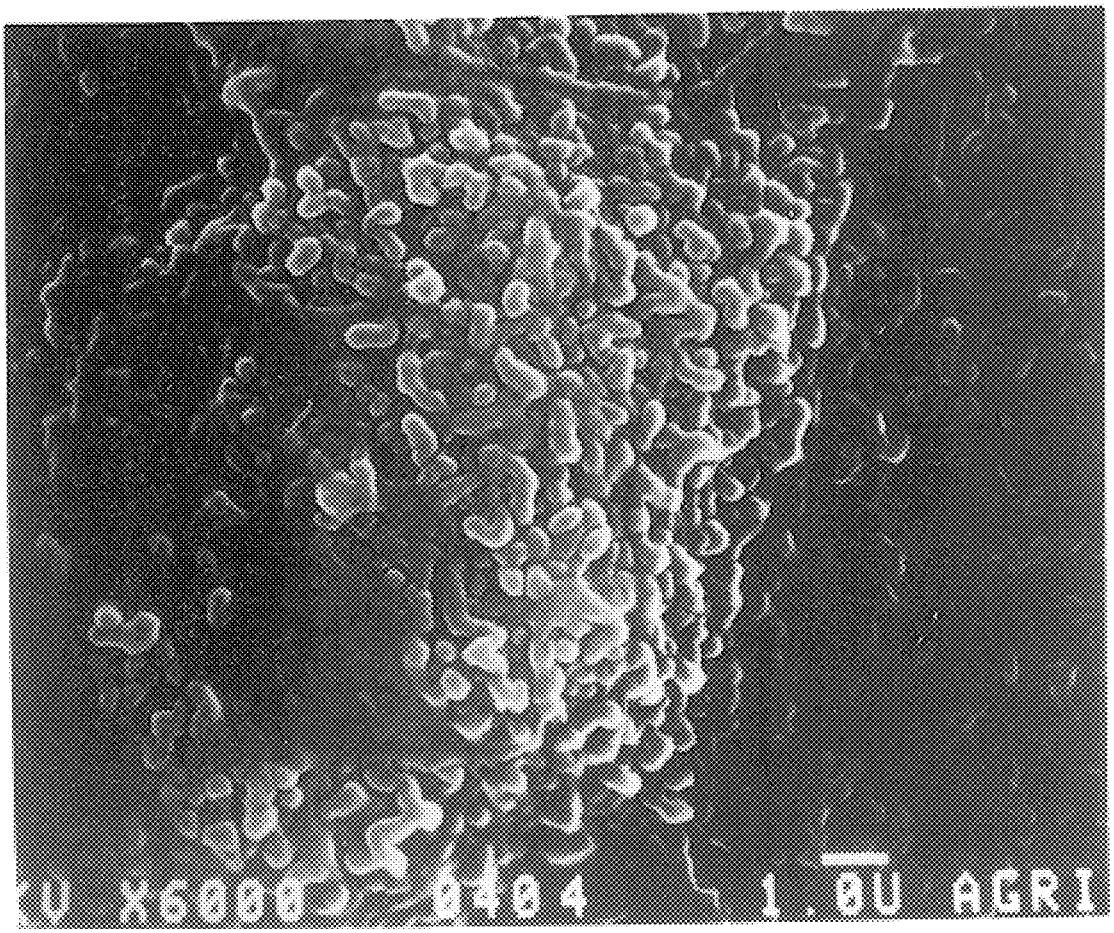
FIG. 2 is a scanning electron micrograph (SEM) of a clot effected by a commercial product.
Figure 3:
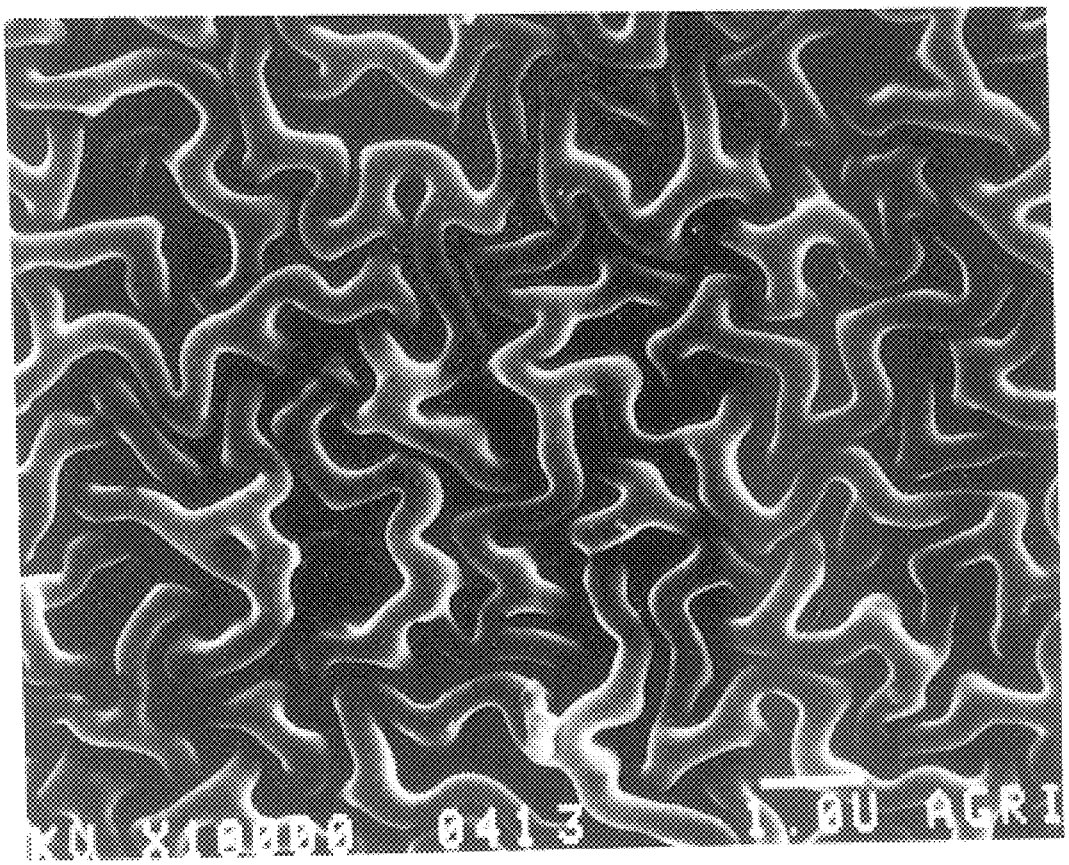
FIG. 3 is a SEM of the clot effected by the product of the invention.

FIG. 2 shows a scanning electron micrograph (SEM) of the clot which built up the commercial product "Tisseell" and FIG. 3 shows a SEM of the product of the invention. The more regular pattern of fibrin polymer of FIG. 3 is to be noted compared to the irregular pattern of FIG. 2 created by the commercial product.

DESCRIPTION OF THE PREFERRED EMBODIMENTS

Preferably, in the fibrin glue of the invention a high molecular substance is added. This substance has gelling properties and promotes also wound healing thus, providing the fibrin glue with valuable properties. The high molecular substance having gelling properties preferably is an organic polymeric material derived from natural sources like glycosamino glycanes preferably components of the connective tissue. Preferably, hyaluronic acid or its pharmaceutically acceptable salts are used as the substance having gelling properties to be present in a two component fibrin glue.

The preferred substance having gelling capability which is hyaluronic acid is a compound having a molecular weight within the range of 50,000 to $8 \times 10^6$ depending on the source, method of preparation and determination. The compound is described in the Merck Index, 11. edition, page 751, reference no. 4675. Its sodium salt is commercially available and has been used as surgical aid in ophthalmological surgery.

Commercially available cryoprecipitate can be used for preparation of the fibrin glue of the invention. However, it can be advantageous to concentrate the cyroprecipitate between a factor 2 and 5, preferably factor 3.

The cryoprecipitate can be obtained from the patient himself by donating an autologous blood unit prior to the operation. This approach prevents the risk of transmission of viral infections by blood derivatives. This way of preparing a fibrin glue is expensive and tedious and cannot satisfy the amount of fibrin glue demaned in the medical art.

In order to obtain a proper commercial product and process, the cryoprecipitate for use in the invention has to become virus-inactivated. A procedure for virus-inactivation is described in PCT/EP 91/00503. The basic principle is treatment of the cryoprecipitate with special detergents and removing the detergent later from the cryoprecipitate.

Tranexamic acid is preferably present in amounts of 10 to 200 mg/ml, more preferred 25 to 100 mg/ml (final concentration). In this concentration range tranexamic acid is as efficient as the aprotinin having an activity of 3,000 to 10,000 KIU/ml. Advantageously, a fibrin glue having tranexamic acid instead of aprotinin seems to be more efficient also in wound healing. An advantage of the fibrin glue of the invention having tranexamic acid is the fact that the concentration of tranexamic acid changes with time at which it is desired that the adhesive has to disintegrate. This time varies according to the various indications and can be balanced by a content of tranexamic acid in the glue in the range of 5 to 100 mg/ml (initial concentration). Tranexamic acid seems also to have a positive influence on the tensile strength by increasing it.

The preferred substance having gelling properties the glycosamino glycan hyaluronic acid to be used in the present invention, preferably has a molecular weight between $10^5$ to $3.6 \times 10^6$ and should be employed in a concentration range up to 1%, preferably up to 0.5%. Preferred is the use of low molecular weight hyaluronic acid in the glue since low molecular weight hyaluronic acid maintains or increases elasticitiy and tensile strength of the clot. However, high molecular weight hyaluronic acid decreases tensile strength of the respective clot. Low molecular weight hyaluronic acid is a hyaluronic acid having a molecular weight range of 400.000 to 1.000.000 Dalton.

The adhesive having, for example, hyaluronic acid shows improved properties probably due to the high surface tension and the relatively high viscosity of hyaluronic acid. For example, when conventional fibrin glue is sprayed during surgery some of the glue leaks to the sides and is suctioned by assistant surgeons or is absorbed in pads and towels. However, the fibrin glue having for example hyaluronic acid stays where it has been sprayed. The adhesive without this ingredient tends to dry and may then turn into a hard and knife-sharp clot which may injure tissues in motion. Contrary to this behaviour of conventional fibrin glue, the adhesive having, for example, hyaluronic acid stays moist and flexible for several days until its disappearance. The disappearance is caused by endogenous proteases. The time of disappearance of the clot can be balanced by the amount of protease inhibitor such as tranexamic acid present in the clot.

A further advantage using hyaluronic acid is due to the fact that the fibrin clot formed does not show as much non specific adhesion to other parts of the body. This means that the clot itself formed by the fibring glue of the invention reduces the adherence of adhesion to the surrounding tissue. This is demonstrated by injecting hyaluronic acid containing fibrin glue into the peritoneal cavity of an experimental animal. Conventional fibrin glues, however, show increasing appearance of intestinal adhesions following surgery.

Another advantage of using a moisture keeping substance having gelling properties, e. g. glycosamino glycanes such as hyaluronic acid, is the feature that the addition of various antibotic preparations to the adhesive such as gentamicin, amoxycillin, ampicillin, cephamezine, ceffazidine in concentrations of 4 to 15 μm or less as well as coliracin at a concentration of about 70 μm or less results in a release of the respective antibiotic from the adhesive. This is particularly of great relevance in surgery of an infected area or in orthopedic surgery, abdominal surgery, skin grafts, etc.

If hyaluronic acid is used as gelling agent a molecular weight of 300,000 to $3.6 \times 10^6$ would be preferred.

Preferably, the concentration range of hyaluronic acid is from 0.1 to 2%. The molecular weight and the concentration can be balanced due to the field of application. For example, in intra-ocular use an agent having gelling properties exhibits higher molecular weight, e.g. hyaluronic acid with a molecular weight of $3.6 \times 10^6$. For bone grafts when hydroxyapatite granules are added to the adhesive it is preferred to use e. g. hyaluronic acid having a molecular weight of 1 to $2 \times 10^6$ at a concentration of about 0.4% for obtaining a uniform distribution of the hydroxyapatite in the adhesive. For use in hemostasis it is more preferred to use low molecular weights of the substance having gelling properties, e. g. hyaluronic acid of about 500,000 molecular weight, where the addition of the gelling agent such as hyaluronic acid. Then, a low concentration preferably in the range of 0.05 to 0.1% causes a sufficiently high surface tension for an almost instantaneous adhesion of the adhesive to the sprayed tissues and prevents leakage of the adhesive to unnecessary and unwanted areas.

The second component, component B, of the fibrin glue of the present invention is prepared by a solution of a proteolytic enzyme being capable of cleaving specifically fibrinogen. Usually thrombin has been used which was isolated from plasma of human beings or mamals such as bovine. This thrombin can be delivered in a lyophilized form. The reconstitution of thrombin occurs with a 40 mmol solution of calcium chloride. The preferred concentration of thrombin is 50 to 200 u/ml. It is preferred to use virus inactivated thrombin portions.

For preparing a fast fibrin glue a thrombin solution of roughly 100 u/ml of a calcium chloride solution will be prepared. For preparing a slow glue for example by filling of cavities, i. e. tooth extraction or sealing the cavity of transphenoided hypophysectomy the thrombin will be further diluted to a concentration of 25 u/ml with the appropiate calcium chloride solution.

Another preferred embodiment of the present fibrin glue comprises as component B a proteolytic enzyme which is isolated from snake venom. This embodiment is advantageous because also patients having developed antibodies against thrombin can be treated. Moreover, patients which are pretreated with heparin can be treated with the fibrin glue according to the invention, because heparin does not influence the reaction of the snake venom enzyme. In a preferred embodiment of the present invention there is used the snake venom enzyme batroxobin which can be isolated from the South American pit viper *Bothrpos moujeni*. Preferably component B contains 0.5 to 10 u/ml of the respective proteolytic enzyme of snake venom, if the snake venom enzyme is used instead of thrombin.

Chemically batroxobin is a single chain glycopeptide with a molecular weight of approximately 36,000. Defibrase$^R$ causes cleavage of α 16 Arg/17 Gly bound in fibrinogen which causes the release of fibrinopeptide A and the formation of monomeric fibrin I.

In the fibrin glue of the invention also purified fibrinogen, fibronectin and factor XIII can be used as component A. The risk of after-bleeding is then reduced.

If proteolytic proteases from snake venom are used for the preparation of component B, also "conventional" components A having fibrinogen, fibronectin and factor XIII would be used. A preferred embodiment is the combination of the component A of the invention derived from cryoprecipitate with tranexamic acid and the component B of the invention having the proteolytic enzyme isolated from snake venom.

The process for preparing the fibrin glue of the invention having tranexamic acid and/or a substance with gelling properties comprises the steps of manufacturing component A comprising the steps of preparing a cryosolution from cryoprecipitate, a virus inactivation, the removal of virucidal agent, the addition of tranexamic acid and/or substance with gelling properties preparing an appropriate protease-solution.

Preferably a cryopaste is prethawed over night at 4 to 10° C. The cryopaste is dissolved in a buffer containing sodium chlorid trisodium citrate and glycin and having a pH of 7.0 to 7.2 and than heated to 30 to 35° C. The cryopaste should dissolve readily. The dissolution can be speeded up by cutting the cryopaste in small pieces after thawing. After cooling the solution to almost room temperature and adjusting the pH to a value of 7.0 to 7.2 aluminiumhydroxid is added under stirring. The precipitate is centrifuged and discarded. Optionally a filtration step is carried out. Then calcium chloride is added up to the desired final concentration of calcium chloride.

For the virus inactivation the solution is heated up to 30° C. Then the detergents are added. Other stirring for some time the solution is transferred into a virus free container and left at slightly elevated temperatures for several hours without stirring.

The virucidal agents are removed by adding an amount of ricine oil and gently stirring for several minutes. When the oil-/water-phases have been seperated the solution is cooled to room temperature. The aqueous layer is withdrawn in a virussafe container and the oillayer is discarded. The aqueous layer is clarified by filtration.

The pH must be checked to be 7.0 to 7.2. Then the protein solution is pumped through a reversed phase column at ambient temperature. After having measured the protein content (in the range of 10 to 60 mm/ml the eluate is concentrated by ultrafiltration to a protein content of 60 to 100 mg/ml and dialysed against a buffer which is identical to the buffer mentioned above but having additionally a relatively high concentration of calcium chloride. Then the tranexamic acid and/or the gelling agent or pharmaceutically acceptable salts thereof are added. A sterile filtration is carried out and the sample is filled and deep frozen in suitable containers.

The anti fibrinolytic agent tranexamic acid must not be jointly lyophylized with the clotting active component but can be added separately. This is advantageous since the cryopreparations can be concentrated markedly, e. g. at least by a factor of 3. The anti fibrinolytic agent can be added independently from the type of the protease preparation of component B to be constituted from thrombin or snake venoms.

Component B is preferably a freeze dried protease. Particularly preferred is lyophilized thrombin or lyophilized fraction of the South American pit viper *Bothrpos moujeni*. The proteolytic enzyme is known under the tradename Reptilase and is the enzyme batroxobin.

The proteolytic enzymes are dissolved in a calcium chloride buffer.

Alternatively, the substance having gelling properties is admixed to component B. It may be admixed also in both components A or B.

The application of the two components A and B is preferably performed using a double syringe technique for example through a plastic connector. Upon mixing of the two components a clot will be formed. The application can occur via a canula or may be sprayed to a three lumen catheter. Each one of the two components is injected into a separate lumen and an air pressure source in the range of some atmospheres is connected to the third lumen in order to spray the mixture.

The fibrin glue of the invention is advantageous because it can be used with patients having severe blood coagulation disorders and being still cheaper than the known fibrin glues. Patients with severe hemophilia can subsequently, for example undergo tooth extractions without preventive infusions of factor VIII concentrates with a success rate of over 80%. This means only about one fifth of the patients need infusions due to post-extraction bleeding. Moreover, such patients who are pretreated with heparin can be treated with the fibrin glue of the invention. Another advantage is that people who raised antibodies against thrombin the second component of the fibrin glue can be treated with a fibrin glue according to the invention wherein thrombin is substituted by a protease from snake venom especially Defibrase$^R$ which is the serine protease batroxobin isolated from the venum of the South American pit viper *Bothrpos moujeni*.

Human fibrinogen (grade L) was from Kabi (Stockholm), bovine thrombin from Merz-Dade. Chromogenic substrate N-a-benzoyl-DL-arginine-p-nitroanilide (BAPNA) and analytic grade reagents were from Sigma (St. Louis, Mo.). Reagents and salts were diluted with 0.015 M Tris, 0.15 M NaCl, with pH 7.4. Fibrinogen was dialyzed in Tris buffer with concentration determined from $Abs_{280}$ using a conversion factor of $E^{1\%}280=15$.

Bovine thrombin was from commercial sources (Merz-Dade or Parke Davis) with activity rating by the manufacturer. Reptilase$^R$, a snake venom which only releases FPA, was from Pentapharm (Basel). The proteolytic activity of Reptilase$^R$ was normalized to that of thrombin by comparing their rates of proteolysis of a non-specific chromogenic substrate BAPNA (0.25 mM) at 37° C., in Tris/saline, pH 8.0, monitored at 405 nm for 15 minutes. On the basis of their esterolytic activity, the unit activity of the reptilase was normalized to that of thrombin.

Fibrin glue was essentially generated by a dual syringe method with pure or cryoprecipitate fibrinogen substrate in one syringe, and reptilase (20 U/ml) or thrombin with $CaCl_2$ (20 mM) in the other.

Clotting time (CT) was determined with a Research Model 300-R ACL Coagulation Analyzer (IL, Milan). Viscoelasticity (TEG) was determined on a 3-channel Heiliger Thromboelastograph at 37° C. Breaking strength (BS) of glues (in grams) was determined by mixing the glue components between two pieces of coarse weaved, synthetic fiber (0.5×1 cm), allowing the formation of gel totally interweaved between the two pieces of coarse mesh and after 2 hours at 24° C. the ensemble of mesh-glue-mesh pulled apart using an Accuforce Cadet Tensionometer (AMATEK, Mansfield & Greene, USA).

Sterile cryoprecipitate (cryo) was prepared from frozen (−30° C.) human plasma which was thawed at 4° C. and the supernatant plasma removed. Five such units were pooled to determine protein and fibrinogen concentrations was determined by the Biuret method before and after clotting the cryoprecipitate (diluted 1:5) with 2 U/mL thrombin. Factor XIII was determined by measuring [$^3$H]-putrescine incorporation into dimethylated casein after activation of the samples with 4 U/mL bovine thrombin, 10 min, 22° C.

A notable feature of a typical CT-fibrinogen curve is that it is biphasic for a fixed level of thrombin or reptilase and reaches a minimum in the 1–8 mM fibrinogen range. This differs somewhat from the maximal turbidity (after 10 min) which peaks in the range 20 to 40 mM fibrinogen. A converse experiment shows the dependence of CT on either thrombin or reptilase levels. This curve shows a near linear inverse dependence of gelling rate at low enzyme levels (less than 2 U/mL), which plateaus above at higher levels.

The development of viscoelasticity of pure fibrin is somewhat slower than its turbidity. Ca(II) is a major cofactor in gel reinforcement through factor XIIIa-induced covalent interlocking of protein chains. Such gel crosslinking is a major source of mechanical strength of the gel, which plateaus after 20 min.

A note about the ability of reptilase to induce factor XIIIa activity seems appropriate.

Protein Levels of pooled cryoprecipitate:

Pooled cryo prepared from 5 units, gave the following mean values:

Protein: 75 mg/mL

Fibrinogen: 36 mg/mL

Factor XIII: 4.10 U/mL

Coagulation rates

The clotting time (CT) of cryo is linearly dependent on thrombin or reptilase levels. However, above 3 U/ml, increasing enzyme levels exert little effect on CT. For a fixed level of enzyme, serial dilution of cryo, gives a biphasic CT-curve equivalent to the fibrinogen-dependency noted in the pure fibrin system.

Viscoelasticity (TEG) and Breaking Strength (BS) of Cryo Glues.

The development of viscoelasticity of cryo glues was investigated with either thrombin or reptilase. This parameter takes much longer to develop than turbidity. However, cryo glues prepared with excess of $CaCl_2$ and either thrombin or reptilase achieve equivalent TEG values in roughly the same time frame. It seems that after the initial onset of gelation, factor XIIIa-induced cross-linking bolsters the gel fiber structure, so that the TEG values for both glues converge within 1 hour. Similarly with the final BS of both cryo glues formed with an excess of $CaCl_2$. Both cryo glues break at 50 to 60 g. These experiments indicate that the gel fibers within the glue become reinforced by factor XIIIa-induced, covalent cross-linking.

Preparation of a cryo-solution. Commerically cryopaste is prethawed over night at 4 to 10° C. One kilo of the cryo is dissolved in two liters of buffer A (120 mM/l NaCl, 10 mM/l trisodiumcitrate, 120 mM/l glycin and pH 7.0 to 7.2) and preheated to 30 to 35° C. The cryopaste should dissolve readily otherwise it is not suitable for the preparation. In order to speed up the dissolution, cut the cryopaste in small pieces after thawing. Then the solution is cooled to 20° C. to 22° C. and the pH is checked. Optionally it must be adjusted to pH 7.0 to 7.2 by adding diluted sodiumhydroxid or acidic acid. 100 ml aluminiumhydroxide is added and stirred for another 30 minutes. The precipitate is centrifuged and discarded. The supernatant is filtrated using a 1 µm filter. 0.1 M/l $CaCl_2$ is added to render a final concentration of $Ca^{2+}$ of 1 mM/l. Again the pH must be checked.

Virus inactivation

The solution is heated up to 30° C. 1% w/v TNBP and 1% w/v Triton X 100 is added. The mixture is gently stirred for ½ hour. The solution is than transferred into a virusfree container and left at 30° C. for 3½ hours without stirring.

Removal of Virucidal Agents 150 ml Ricine oil is added to the mixture prepared as described above and stirred gently for 30 minutes. While waiting for the oil/water separation (30 to 45 minutes) the solution is cooled to 20° C. The aqueous layer is withdrawn into a virussafe container whereas the oillayer is discarded. The aqueous layer is clarified by filtration on 1 µm/0.45 µm filter cascade. The protein solution is than pumped through a reversed phase column (C-18-Column) at a rate of 3 liter/h at ambient temperature. The throughput is monitored by UV and collected until the absorbance has returned to 50%. The fraction contains roughly 40 mg/ml as measured in a protein assay.

The eluate is concentrated by diafiltration to a protein content of 70 to 80 mg/ml and dialyse against sufficient amount of a buffer B (same ingredients as buffer A but additionally 1 mM/l calcium chloride). Then tranexamic acid or its pharmaceutically acceptable salts in amounts of 10 to 200 mg/ml solution (final concentration in component A) is added. Afterwards a sterile filtration carried out using a 0.45 μm+0.2 μm cascade. The solution is then filled and deep frozen in plastic bags, optionally lyophilized.

Preparation of a thrombin solution

Lyophilized thrombin is dissolved in a solution of 40 mM/L calcium chloride. The amount of thrombin is 100 U/ml in the glue. For a fast working glue, for example for spraying of the glue to the area of the wound, a thrombin solution of 100 U/ml in calcium chloride will be sufficient. For a slow glue, for example filling of cavities during a tooth extraction or sealing the cavity of transphenoided hypophisectomy the thrombin will be further dissolved to a final concentration of 3–5 U/ml by adding great amounts of $CaCl_2$.

The thrombin solution is virus inactivated by methods known to the skilled person.

The preparation of reptilase is similar to that of thrombin. However, the amount of reptilase is roughly 2 U/ml.

The substance having gelling properties can be added to both components A or B. In a typical preparation hyaluronic acid or its pharmaceutically acceptable salts is dissolved in a buffer of component A and B yielding a concentration of 0.1 to 2% depending of the field of application.

We claim:

1. A component useful in a fibrin glue for human application comprising:

i) a virus-inactivated and concentrated cryoprecipitate that contains fibrinogen, and ii) tranexamic acid or a pharmaceutically acceptable salt, thereof.

2. A two-component fibrin glue for human application comprising:

a) component A, comprising the component of claim 1, and b) component B, comprising a proteolytic enzyme that, upon combination with component A, cleaves, specifically, fibrinogen present in the cryoprecipitate of component A, thereby, effecting a fibrin polymer.

3. The two-component fibrin glue of claim 2, further comprising in component A a substance having wound-healing properties and/or gelling properties.

4. The two-component fibrin glue of claim 3, wherein the substance is a muco-polysaccharide.

5. The two-component fibrin glue of claim 4, wherein the muco-polysaccharide is hyaluronic acid.

6. The two-component fibrin glue of claim 2, wherein the proteolytic enzyme in component B is thrombin.

7. The two-component fibrin glue of claim 6, wherein the thrombin is obtained from a mammal.

8. The two-component fibrin glue of claim 7, wherein the thrombin is obtained from a human.

9. The two-component fibrin glue of claim 2, wherein the proteolytic enzyme in component B is obtained from snake venom.

10. The two-component fibrin glue of claim 9, wherein the proteolytic enzyme is batroxobin obtained from the venom of the South American pit viper *Bothrpos moujeni*.

11. The two-component fibrin glue of claim 2, wherein component A contains fibrinogen, fibronectin, factor VIII, and tranexamic acid.

12. The two-component fibrin glue of claim 2, wherein the proteolytic enzyme in component B is obtained from snake venom.

13. The two-component fibrin glue of claim 12, wherein the proteolytic enzyme is thrombin or obtained from snake venom.

14. The two-component fibrin glue of claim 13, wherein proteolytic enzyme obtained from the snake venom is batroxobin obtained from the venom of the South American pit viper *Bothrpos moujeni*.

15. A process for making the component of claim 1, comprising the steps of:

preparing a cryo-solution of cryoprecipitate, virus-inactivating the cryo-solution, removing virucidal agents from the cryo-solution to effect an eluate, ultrafiltration of the eluate to effect a concentrate, adding to the concentrate tranexamic acid, a substance having gelling properties, a combination of tranexamic acid and a substance having gelling properties, or a pharmaceutically acceptable salt or salts thereof.

16. A process for making a two-component fibrin glue for human application comprising the steps of:

conducting the process of claim 15, to effect a component A, and obtaining, as a component B, a proteolytic enzyme that, upon combination with component A, cleaves, specifically, fibrinogen present in the cryoprecipitate of component A, thereby, effecting a fibrin polymer.

17. The process of claim 16, further comprising the step of adding to component A a substance having gelling and/or wound healing properties.

18. The process of claim 17, further comprising the step of wherein the substance is a muco-polysaccharide.

19. The process of claim 18, wherein the muco-polysaccharide is hyaluronic acid.

20. The process of claim 16, wherein the proteolytic enzyme in component B is thrombin.

* * * * *